(12) United States Patent
Kolberg

(10) Patent No.: US 11,317,785 B2
(45) Date of Patent: May 3, 2022

(54) ENDOSCOPE HEAD AND ENDOSCOPE PROVIDED THEREWITH

(71) Applicant: DIGITAL ENDOSCOPY GmbH, Friedberg (DE)

(72) Inventor: Stefan Kolberg, Friedberg (DE)

(73) Assignee: DIGITAL ENDOSCOPY GMBH, Friedberg (DE)

( * ) Notice: Subject to any disclaimer, the term of this patent is extended or adjusted under 35 U.S.C. 154(b) by 246 days.

(21) Appl. No.: 16/349,388

(22) PCT Filed: Nov. 21, 2017

(86) PCT No.: PCT/EP2017/079876
§ 371 (c)(1),
(2) Date: May 13, 2019

(87) PCT Pub. No.: WO2018/095894
PCT Pub. Date: May 31, 2018

(65) Prior Publication Data
US 2019/0328215 A1    Oct. 31, 2019

(30) Foreign Application Priority Data
Nov. 22, 2016    (DE) .......................... 102016122477.4

(51) Int. Cl.
*A61B 1/00*    (2006.01)
*A61B 1/005*    (2006.01)
(Continued)

(52) U.S. Cl.
CPC ........ *A61B 1/00098* (2013.01); *A61B 1/0057* (2013.01); *A61B 1/273* (2013.01); *A61B 8/12* (2013.01)

(58) Field of Classification Search
CPC ............ A61B 1/00098; A61B 1/00101; A61B 1/00135; A61B 1/00137; A61B 1/00142;
(Continued)

(56) References Cited

U.S. PATENT DOCUMENTS 5,562,600 A    10/1996  Matsuno
5,569,157 A *  10/1996  Nakazawa ......... A61B 1/00165
                                                    600/106
(Continued)

FOREIGN PATENT DOCUMENTS

DE    102012009332 A1    11/2013
EP       0142573 A1     5/1985
(Continued)

OTHER PUBLICATIONS

U.S. Appl. No. 16/087,903 to Stefan Kolberg, filed Sep. 24, 2018.
(Continued)

*Primary Examiner* — Ryan N Henderson
(74) *Attorney, Agent, or Firm* — Greenblum & Bernstein P.L.C.

(57) ABSTRACT

The invention relates to an endoscope head including an endoscope head body in which at least one working channel is formed, wherein a pivotable Albarran lever is provided distally of the distal end of the working channel, wherein, on the endoscope head body, a pivot member actuatable from the proximal side is provided for pivoting the Albarran lever, wherein a pulling wire channel extends in the endoscope head body and has a pulling wire for actuating the pivot member guided therein, wherein the pivot member has a protrusion, and wherein the pulling wire is capable of displacing a sliding member having a surface on which the protrusion is supported, so that the pivot member is rotated by displacing the sliding member.

9 Claims, 4 Drawing Sheets

(51) Int. Cl.
*A61B 1/273* (2006.01)
*A61B 8/12* (2006.01)

(58) Field of Classification Search
CPC ... A61B 1/0008; A61B 1/0052; A61B 1/0057; A61B 1/00183; A61B 8/00; A61B 8/12; G02B 23/24; G02B 23/2476
See application file for complete search history.

(56) References Cited

U.S. PATENT DOCUMENTS

| | | | |
|---|---|---|---|
| 10,856,724 B2 * | 12/2020 | Miller | A61B 1/00089 |
| 11,019,984 B2 * | 6/2021 | Miller | A61B 1/00133 |
| 2016/0089004 A1 | 3/2016 | Morimoto | |
| 2016/0206180 A1 * | 7/2016 | Hosogoe | A61B 8/0841 |
| 2016/0270630 A1 * | 9/2016 | Tanaka | A61B 1/00098 |
| 2016/0270633 A1 * | 9/2016 | Iwasaka | A61B 1/00098 |
| 2016/0270634 A1 * | 9/2016 | Tanaka | A61B 1/00098 |
| 2016/0270635 A1 * | 9/2016 | Tanaka | A61B 1/00098 |
| 2016/0270636 A1 * | 9/2016 | Iwasaka | A61B 1/00137 |
| 2016/0270637 A1 * | 9/2016 | Tanaka | A61B 1/00098 |
| 2017/0000316 A1 | 1/2017 | Sueyasu | |
| 2017/0000317 A1 * | 1/2017 | Iizuka | A61B 1/0615 |
| 2017/0020370 A1 * | 1/2017 | Yamaya | A61B 1/00142 |
| 2017/0112362 A1 * | 4/2017 | Morimoto | A61B 8/12 |
| 2017/0238789 A1 * | 8/2017 | Iizuka | A61B 1/018 |
| 2018/0092512 A1 * | 4/2018 | Hiraoka | A61B 1/00 |
| 2018/0185045 A1 * | 7/2018 | Ohki | A61B 1/00098 |
| 2018/0206708 A1 * | 7/2018 | Miller | A61B 1/00101 |
| 2018/0249894 A1 * | 9/2018 | Kolberg | A61B 1/018 |
| 2018/0279857 A1 * | 10/2018 | Miller | A61B 1/00131 |
| 2019/0223697 A1 * | 7/2019 | Hosogoe | A61B 1/0014 |
| 2019/0223698 A1 * | 7/2019 | Hosogoe | A61B 1/00098 |
| 2020/0178767 A1 * | 6/2020 | Miller | A61B 1/00142 |
| 2020/0178773 A1 * | 6/2020 | Miller | A61B 1/2736 |
| 2020/0337530 A1 * | 10/2020 | Miller | A61B 1/00105 |

FOREIGN PATENT DOCUMENTS

| | | |
|---|---|---|
| JP | H08-56900 A | 3/1996 |
| JP | 2007-029291 A | 2/2007 |
| JP | 2014-128465 A | 7/2014 |
| JP | 5970144 B1 | 8/2016 |

OTHER PUBLICATIONS

U.S. Appl. No. 16/315,422 to Anh Minh Do, filed Jan. 4, 2019.
U.S. Appl. No. 16/328,580 to Anh Minh Do, filed Feb. 26, 2019.
International Search Report International Patent Application No. PCT/EP2017/079876, dated Mar. 15, 2018.
Office Action issued in China Counterpart Patent Appl. No. 201780070718.X, dated Apr. 25, 2021.
Second Office Action issued in China Counterpart Patent Appl. No. 201780070718.X, dated Nov. 3, 2021.

* cited by examiner

ENDOSCOPE HEAD AND ENDOSCOPE PROVIDED THEREWITH

The present invention relates to an endoscope head and to an endoscope comprising said endoscope head.

Such an endoscope may e.g. be used as a duodenoscope, i.e. an endoscope for examining e.g. the gullet (esophagus) or also the duodenum, the bile duct, the gall bladder, the pancreatic duct, the pancreas, etc. By means of the duodenoscope, it is possible to enter the duodenum through the gullet, the stomach and the pylorus.

The duodenoscope has a sideways-directed (lateral) optical system (illumination means and camera). This may make it difficult to introduce it into the gullet and push it forward through the gullet as a "forward-directed" observation cannot be carried out easily. Sufficient space for bending the distal end of the duodenoscope by about 90° so as to be able to look ahead is only available in the stomach or in the duodenum.

Moreover, at the exit of the working channel, the duodenoscope has an Albarran lever which, by pivoting, allows a targeted deflection of the tools that are pushed through the working channel. Such an Albarran lever is usually pivoted on the distal side of the endoscope by a pulling wire or a control wire.

The installation space in the endoscope head is very limited, among others due to the optical system (illumination means and camera) and its signal and power cables, the working channel and the pulling wire channel.

It is the object of the present invention to provide an endoscope head and an endoscope in which the construction in the distal area is improved with a view to an optimum use of the installation space.

This object is achieved by an endoscope head of the present disclosure. Advantageous further developments (embodiments) are described herein.

Thus, the invention concerns an endoscope head comprising an endoscope head body in which at least one working channel is formed, wherein a pivotable Albarran lever is provided distally of the distal end of the working channel, wherein, on the distal side of the endoscope head body, a pivot member actuatable from the proximal side is provided for pivoting the Albarran lever, wherein a pulling wire channel extends in the endoscope head body and guides a pulling wire for actuating the pivot member, wherein the pivot member has a protrusion, and wherein the pulling wire is capable of displacing a sliding member having a surface on which the protrusion is supported, so that the pivot member is rotated by displacing the sliding member.

For pivoting the Albarran lever, the protrusion of the pivot member is inserted into the sliding member that is operable by the pulling wire. Thus, a movement of the sliding member effected by the pulling wire causes a movement of the pivot member. For realizing the pivoting movement of the Albarran lever, only a small displacement path of the sliding member has to be provided in the endoscope head. In this way, a solution with a minimum space requirement for realizing the pivoting movement of the Albarran lever is created.

The protrusion of the pivot member can have the shape of an involute which is supported on the surface of the sliding member in a rolling manner. In other terms, the protrusion of the pivot member can have the shape of a rolling element. Thus, the protrusion of the pivot member can roll on a surface of the sliding member when the pivot member changes its relative position to the sliding member upon pivoting of the Albarran lever. Thus, the pivot member can be installed to abut on the sliding member, so that the space requirement further decreases. Alternatively, the protrusion of the pivot member can be formed as a sliding or gliding element which is slidingly supported on the surface of the sliding member. In a further alternative, the protrusion of the pivot member can comprise, on a contact portion with the sliding member, a rolling wheel that is rollably supported on the surface of the sliding member.

The sliding member can have a first surface on which a first outer surface of the protrusion is supported, and the sliding member can have a second surface on which a second outer surface of the protrusion is supported. Thus, in every pivoting direction of the Albarran lever, the pivot member can be provided to abut on the sliding member. The pivot member and the sliding member can be provided in permanent contact independently of the position of the Albarran lever.

The sliding member can be configured such that, when the pulling wire is moved in the proximal direction, the first surface of the sliding member has the first outer surface of the protrusion roll thereon in such a way that the pivot member pivots the Albarran lever in the proximal direction and that, when the pulling wire is moved in the distal direction, the second surface of the sliding member has the second outer surface of the protrusion roll thereon in such a way that the pivot member pivots the Albarran lever in the distal direction.

The first surface and the second surface of the sliding member can face each other and the first outer surface and the second outer surface of the protrusion can face in opposite directions.

By means of the pulling wire, the sliding member is displaceable back and forth in the axial direction of the endoscope head. In the endoscope head according to the invention, a translational movement/motion (of the sliding member) is transformed into a rotational movement (of the pivot member). A conventional solution, according to which an arcuate movement of a pulling wire receiving element generated an arcuate movement of the Albarran lever, occupied a comparatively large space in the endoscope head. This conventional solution generated a sinusoidal force path.

According to the invention, only a small axial sliding/displacement path of the sliding member has to be created in the endoscope head for realizing the pivoting movement of the Albarran lever. This contributes to further reducing the space requirement in the endoscope head for realizing the pivoting movement of the Albarran lever. According to the invention, an even more uniform force path is generated when the translational motion (of the sliding member) is transformed into the rotational movement (of the pivot member).

The distal end of the pulling wire channel can be sealed at the endoscope head body. Thus, the possibility of transmitting germs that might settle in the pulling wire channel, is prevented.

The distal end of the pulling wire can be anchored to the endoscope head body, and the sliding member can be arranged at the pulling wire proximally of the anchoring point. The distal end of the pulling wire can contribute to positioning the sliding member. In this way, the space for the sliding member can be open towards the pivot member as no guiding elements for guiding the sliding member have to be provided between the sliding member and the pivot member. The sliding member and the pivot member can be installed still closer to each other.

Furthermore, when the pulling wire is pulled from the proximal side, a pulling wire sleeve connecting the sliding member to the proximal end of the pulling wire channel moves the sliding member relative to the pulling wire in the distal direction. The pulling wire sleeve can be constructed like a Bowden cable sleeve and can be elastic. The pulling wire sleeve can be anchored to the sliding member at the proximal end of the pulling wire channel and at the proximal side of the sliding member.

The above-described aspects of the present invention can be suitably combined.

Below, the present invention will be described in detail by means of embodiments, with reference to the drawings.

EMBODIMENT 1

First of all, a first embodiment of the present invention will be described with reference to FIGS. 1 to 3.

Figure 1:
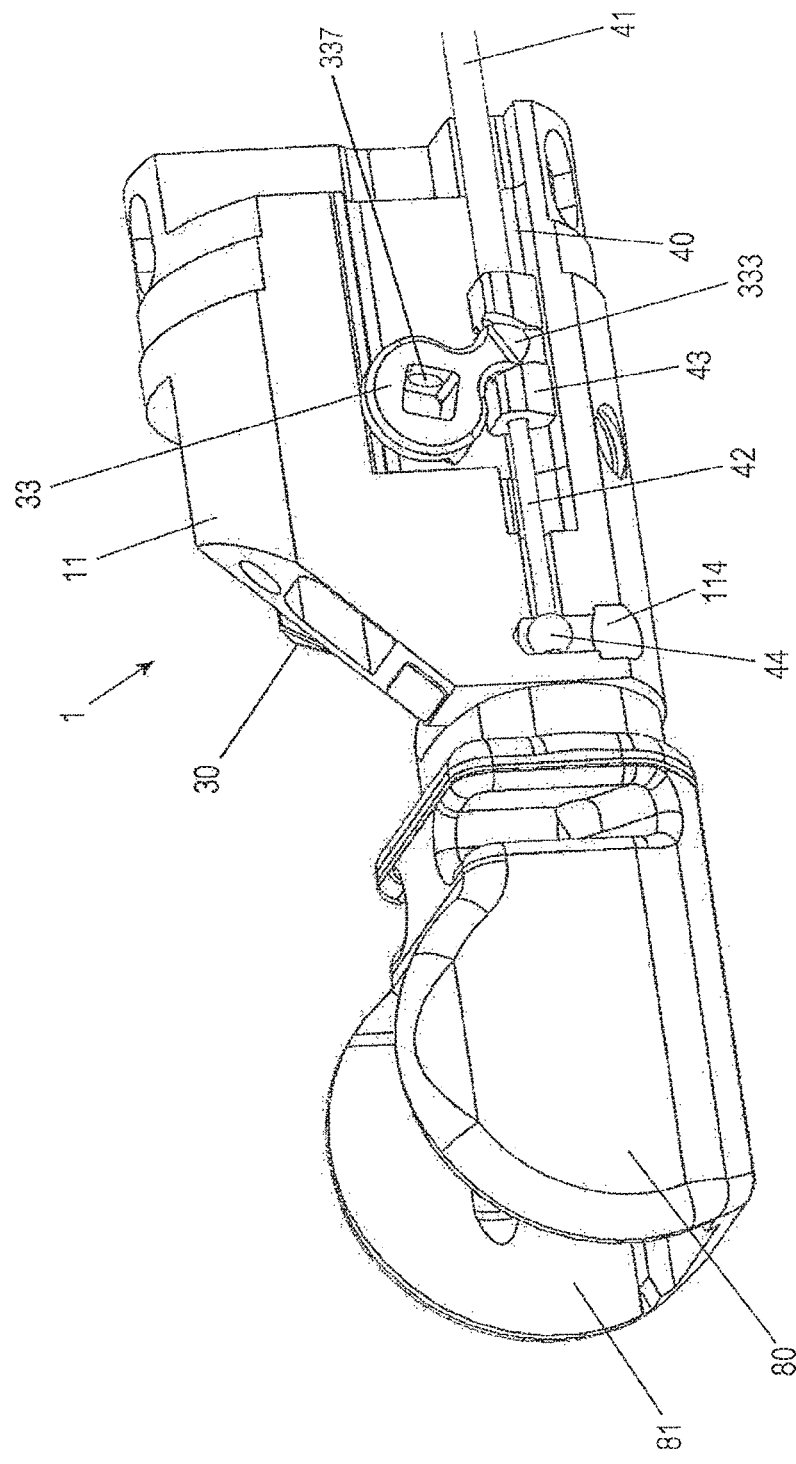
FIG. 1 shows a perspective sectional view of an inventive endoscope head of a first embodiment from the right side.
Figure 2:
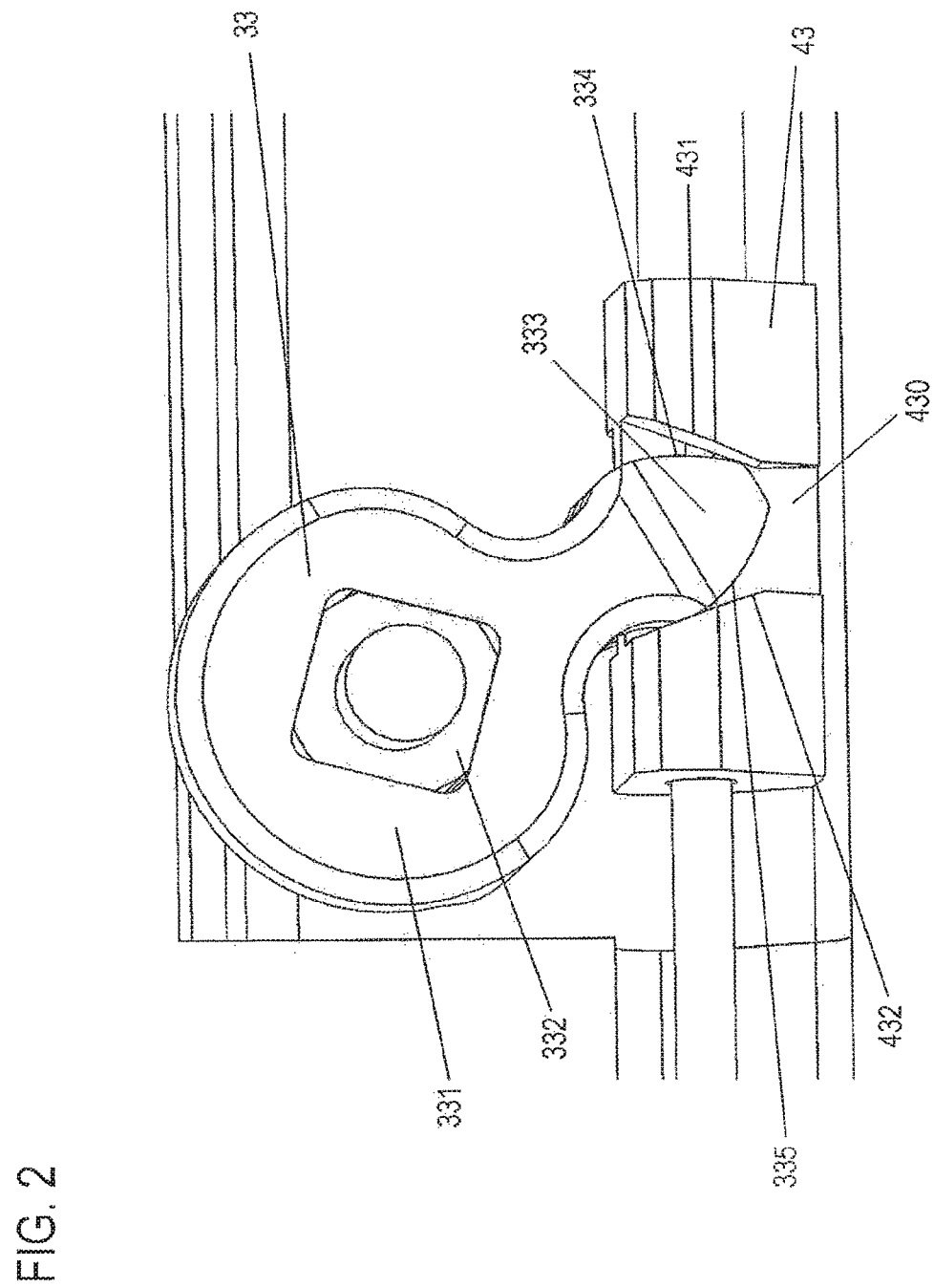
FIG. 2 shows a view of a detail of the inventive endoscope head of the first embodiment from FIG. 1.

FIG. 1 shows a perspective sectional view of an inventive endoscope head 1 of a first embodiment. For improving clarity, the endoscope head 1 is shown in FIG. 1 in a sectional view in order to show several elements (33, 41-44) provided in the endoscope head and their relation to each other in a more comprehensible way.

Figure 3:
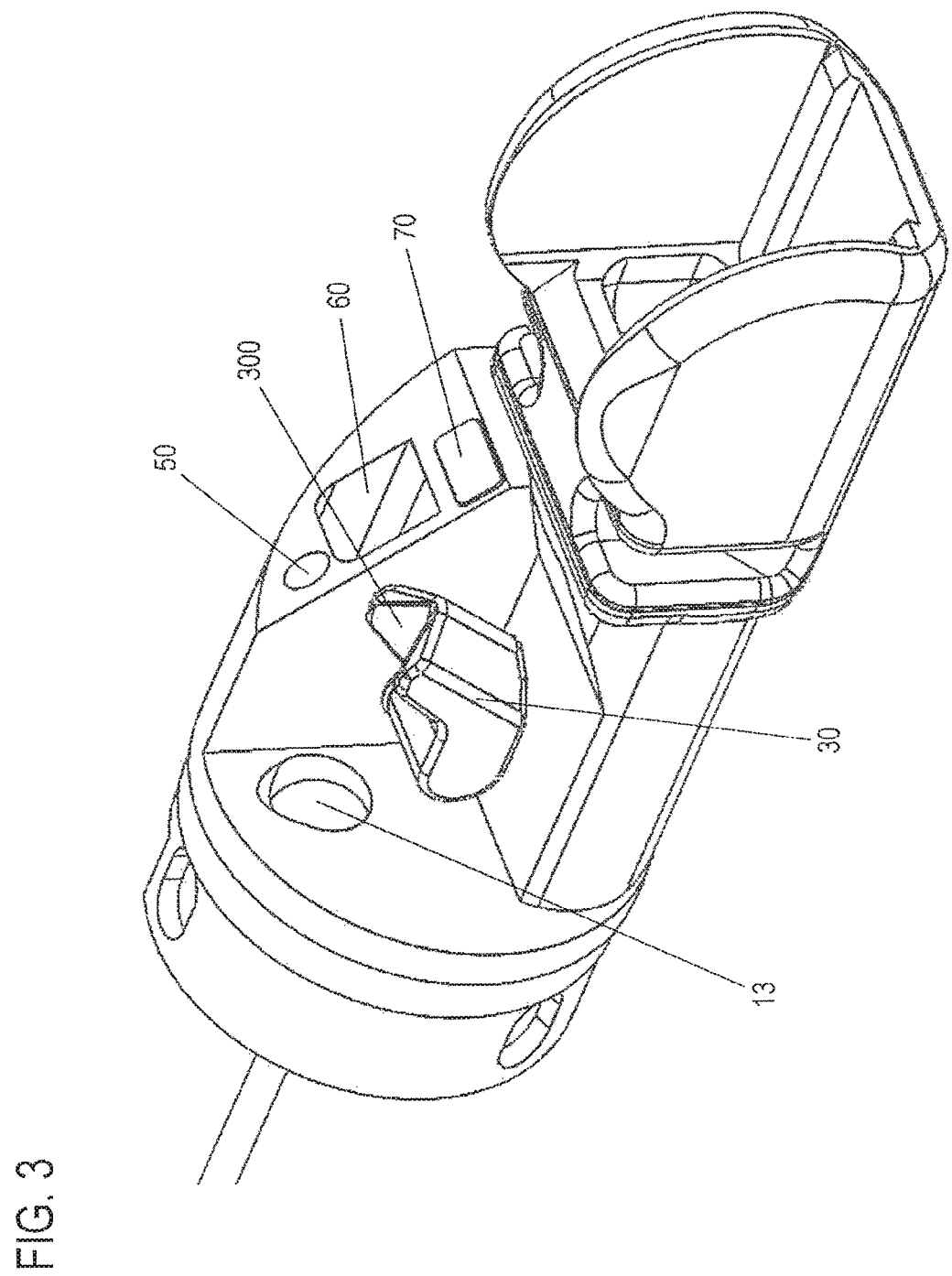
FIG. 3 shows a perspective view of the inventive endoscope head of the first embodiment from the left side.

FIG. 1 shows the endoscope head 1 from the right side, whereas FIG. 3 shows the endoscope head 1 from the left side. Thus, in the present invention, the formulations "right side" and "left side" relate to the representations of FIGS. 1 and 3. Hence, an Albarran lever, which will be described below, is arranged on the left side of the endoscope head 1.

With reference to FIG. 1, the endoscope head 1 comprises an endoscope head body 11, which is arranged at the distal area of an endoscope not shown in any greater detail.

The endoscope comprises an operating member and an insertion portion. The operating member is located at the proximal side and the insertion portion is located at the distal side of the operating member. The operating member comprises a working channel inlet and an adjusting knob for bending an endoscope bending portion at the distal end of the insertion portion of the endoscope. Furthermore, the operating member is provided with a grip portion by which the operator holds the endoscope. The endoscope head 1 according to the invention is arranged at the distal end of the insertion portion.

A working channel 13 (cf. FIG. 3) is formed in the endoscope head body 11 of the endoscope head 1. The working channel 13 extends from the working channel inlet on the operating member to the endoscope head 1. The working channel 13 has a distal outlet opening facing an Albarran lever 30, as is shown in FIG. 3.

The Albarran lever 30 has a working surface 300 which points upwards in the resting position of the Albarran lever 30 as shown in FIG. 1. The resting position of the Albarran lever 30 shown in FIG. 1 is a non-pivoted position of the Albarran lever 30. The working surface 300 is curved inwards, i.e. it is concave.

When a tool guided through the working channel 13, such as a guiding wire, is further advanced in the distal direction, it gets into contact with the working surface 300 of the Albarran lever 30. The working surface 300 can be lifted by pivoting the Albarran lever 30, thereby changing the angle to the distal outlet opening of the working channel 13. In this way, the tool guided in the working channel 13 can be advanced laterally.

The Albarran lever 30 is therefore arranged so as to be pivotable relative to the endoscope head body 11 and, for this purpose, is pivoted by a pivot member. In the first embodiment, the pivot member is formed by a pivot axis element not shown in FIG. 1 (for reasons of clarity) and by a force-receiving element 33. The pivot axis element is rotatably supported on a bearing formed in the endoscope head body 11.

The non-shown pivot axis element is a shaft element and has an end portion with the Albarran lever 30 arranged thereon on its longitudinal end (the left longitudinal end). This (left) end portion is formed such that it is connected in a form-fitting manner to the Albarran lever 30 arranged on said end portion. In the present embodiment, the (left) end portion has a square profile. At its shaft connection, the Albarran lever 30 has a corresponding square profile on its shaft connection, see FIG. 3.

The Albarran lever 30 can be pushed off the (left) end portion of the pivot axis element by being withdrawn from the pivot axis element in the lateral direction (leftwards). The Albarran lever 30 is pushed onto the pivot axis element in a firm clamp fit and can be secured to the pivot axis element by a locking means (bolt, pin, etc.).

At its other longitudinal end (the longitudinal end on the right), the non-shown pivot axis element has an end portion on which the force-receiving element 33 is arranged. Said (right) end portion is formed such that it is connected in a form-fitting manner to the force-receiving element 33 arranged on said end portion. In the present embodiment, the (right) end portion has a square profile. The force-receiving element 33 has a force-receiving-element main body 331 in which an opening 332 for the pivot axis element is formed. The opening 332 for the pivot axis element has a square profile corresponding to the square profile of the (right) end portion of the pivot axis element, see FIG. 1 and FIG. 2. The force-receiving-element main body 331 can be formed with a radial opening 337 into which a locking screw can be inserted. Said locking screw locks the force-receiving element 33 on the pivot axis element. The force-receiving element 33 can be actuated by a sliding member 43 which is operatively connected to a pulling wire 42.

A pulling wire channel 40 is formed in the endoscope head body 11 of the endoscope head 1. The pulling wire channel 40 extends in the axial direction of the endoscope head 1 from a non-shown proximal operating member to the endoscope head 1. A pulling wire sleeve 41, which is constructed as a Bowden cable sleeve, extends in the pulling wire channel 40. The pulling wire sleeve 41 is an elastic tube element and can have, in its tube circumference, a spring element (a coil spring) over its entire axial length. The pulling wire sleeve 41 is attached to the proximal end of the pulling wire channel 40 and extends up to the sliding member 43. The pulling wire sleeve 41 is fastened to the sliding member 43 at the proximal side of the sliding member 43. In this way, the sliding member 43 functions as a part of the pulling wire sleeve 41.

The sliding member 43 comprises an axial borehole in which the pulling wire 42 passes through the sliding member 43. The pulling wire 42 is operated, i.e. drawn or released, by a proximal control element (e.g. joy stick, control wheel, etc.). The pulling wire 42 runs from the proximal control element into the proximal inlet of the pulling wire sleeve 41, passes through the pulling wire sleeve 41 and through the sliding member 43, and projects from the distal side of the sliding member 43. To be more exact, a proximal portion of the pulling wire 42 is provided on a proximal side of the sliding member 43.

Thus, the pulling wire 42 is arranged in the pulling wire channel 40. To be more exact, the pulling wire 42 is arranged in the pulling wire sleeve 41, and is movable in the axial direction relative to the pulling wire sleeve 41.

The sliding member 43 has a quadrangular shape, but the invention is not restricted to this specific shape. The sliding member 43 can be reciprocated in the axial direction in the endoscope head body 11. At least in an area in the endoscope head body 11, the pulling wire channel 40 is therefore formed in a shape and size through which the sliding member 43 can be guided during its reciprocating movement.

Therefore, on the proximal side of the pulling wire channel 40, the control element is arranged as a proximal operating member adapted to draw the pulling wire 42 relative to the pulling wire sleeve 41 as in the case of a Bowden cable. A pulling wire nipple 44 is provided on the distal end of the distal end portion of the pulling wire 42, and is anchored in a blind hole 114 on the endoscope head body 11.

The blind hole 114 is formed as a borehole extending from the outer edge into the interior of the endoscope head body 11. After the pulling wire nipple 44 has been introduced, the blind hole 114 is being sealed by a non-shown plug or another closing means. The pulling wire 42 can be arranged in the endoscope head body 11 such that it is introduced into the pulling wire channel 40 from the proximal side and then the pulling wire nipple 44 is pressed on at the distal end of the pulling wire 42.

Due to the pulling wire 42 passing through the sliding member 43, the sliding member 43 is easily guidable and protected against false positioning.

Below, the force-receiving element 33 and the sliding member 43 will be described in more detail. FIG. 2 shows a detail from FIG. 1, with the force-receiving element 33 and the sliding member 43 being shown in an enlarged view.

On its outer periphery, the force-receiving element 33 has a protrusion 333 which is formed as an involute. The protrusion 333 extends radially from the force-receiving element 33. The protrusion 333 has a flattened shape. The protrusion 333 has a first side surface 334, which is formed as a proximal surface, and a second side surface 335, which is formed as a distal surface. The first side surface 334 and the second side surface 335 are formed on the protrusion 333 as external/outer surfaces and face in opposite directions. The first side surface 334 and the second side surface 335 form cam surfaces, each of which has a central protrusion, as is shown in FIG. 2.

At least on its right side, the sliding member 43 has a recess 430, which works as an opening for the force-receiving element 33. The recess 430 has a first boundary surface 431, which is formed as a proximal surface, and a second boundary surface 432, which is formed as a distal surface. The first boundary surface 431 and the second boundary surface 432 delimit the recess 430 and project in the lateral direction to the right. The first boundary surface 431 and the second boundary surface 432 face each other. To be more exact, the first boundary surface 431 and the second boundary surface 432 are formed in a bent shape such that they increasingly move apart from each other towards the top, as is shown in FIG. 2. Thus, the first boundary surface 431 and the second boundary surface 432 form an opening that expands towards the top. In other words, the first boundary surface 431 and the second boundary surface 432 form an opening expanding towards the force-receiving element 33.

The protrusion 333 is arranged in the recess 430. The size of the protrusion 333 is dimensioned such that the cam shape of the protrusion 333 is at least received in the portion of the recess 430 which expands towards the top. When the protrusion 333 is received in the recess 430, the first side surface 334 is opposite to the first boundary surface 431, and the second side surface 335 is opposite to the second boundary surface 432.

The height of the first boundary surface 431 and the second boundary surface 432 in the lateral direction to the right is preferably slightly larger than the thickness of the flat protrusion 333.

Thus, the first side surface 334 can roll off on the first boundary surface 431, and the second side surface 335 can roll off on the second boundary surface 432.

Below, further elements of the endoscope head body 11 will be described.

As is shown in FIG. 3, a camera element 60 and at least one LED 70 as illumination means are provided at the distal area of the endoscope head body 11. The camera element 60 has an elastic signal line and an elastic power supply line. The at least one LED 70 has at least one elastic power supply line. Said lines can be constructed as a common line and are connected to the operating member at the proximal side of the endoscope. At the proximal side, the operating member is connected to a video processor, a display device and the like.

Furthermore, a rinsing nozzle (water nozzle) 50 can be arranged at the distal region of the endoscope head body 11; by said nozzle, a camera window of the camera element 60 can be rinsed free.

On the endoscope head 1, an ultrasonic element is arranged distally from the endoscope head body 11. For this purpose, an ultrasonic element holder 80 is provided on the distal side of the endoscope head body 11. An accommodation space 81 for a non-shown ultrasonic element is provided in the ultrasonic element holder 80. Furthermore, an elastic signal line and an elastic power supply line for the ultrasonic element end on the ultrasonic element holder 80. The lines for the ultrasonic element extend through the endoscope head body 11 to the operating member.

Application

The proximal operating member (control element) can operate the pulling wire 42 by pressing or pulling the pulling wire 42. When the pulling wire 42 is drawn by the control element, the distance of the pulling wire 42 in the pulling wire sleeve 41 is shortened. In this way, the sliding member 43 is displaced/shifted in the distal direction relative to the pulling wire 42. In other words, as the pulling wire 42 is drawn by the control element, the pulling wire sleeve 41 is pressed in the distal direction relative to the pulling wire 42. Thus, the sliding member 43 can move in the distal direction or in the proximal direction.

When the sliding member 43 is moved in the distal direction, the first boundary surface 431 of the sliding member 43 presses the first side surface 334 of the protrusion 333 in the distal direction. Thus, the protrusion 333 and, together therewith, the whole force-receiving element 33 are rotated such that the pivot axis element of the Albarran lever 30 lifts the Albarran lever 30 off its rest position.

When the sliding member 43 is moved in the proximal direction, the second boundary surface 432 of the sliding member 43 presses the second side surface 335 of the protrusion 333 in the proximal direction. Thus, the protrusion 333 and, together therewith, the whole force-receiving element 33 are rotated such that the pivot axis element of the Albarran lever 30 lowers the Albarran lever 30 towards its rest position.

Effects of the Embodiment

As the sliding member 43 is arranged in the endoscope head body 11 such that it is exclusively movable in the axial direction of the endoscope head body 11, only a space intended for this axial movement of the sliding member 43 has to be provided inside the endoscope head body 11.

When the sliding member 43 moves, the force-receiving element 33 performs a rotation around the pivot axis element of the Albarran lever 30. When doing so, the protrusion 333 of the force-receiving element 33 is moved. As said protrusion 333 is seated in the opening 430 of the sliding member 43, the space to be provided inside the endoscope head body 11 for the movement of the protrusion 333 is very small.

Therefore, the elements which realize the pivoting of the Albarran lever 30 in the present invention take up a very small space in the endoscope head body 11.

The space in the endoscope head can be used for other purposes. Moreover, this gives rise to possibilities of reducing the diameter of the endoscope head.

EMBODIMENT 2

Below, a second embodiment of the present invention will be described reference to FIG. 4.

In the first embodiment, the Albarran lever 30 is disposed on a shaft element such that it can be pulled off laterally (to the left). In the second embodiment, a non-shown Albarran lever can be pulled off towards the distal side.

Figure 4:
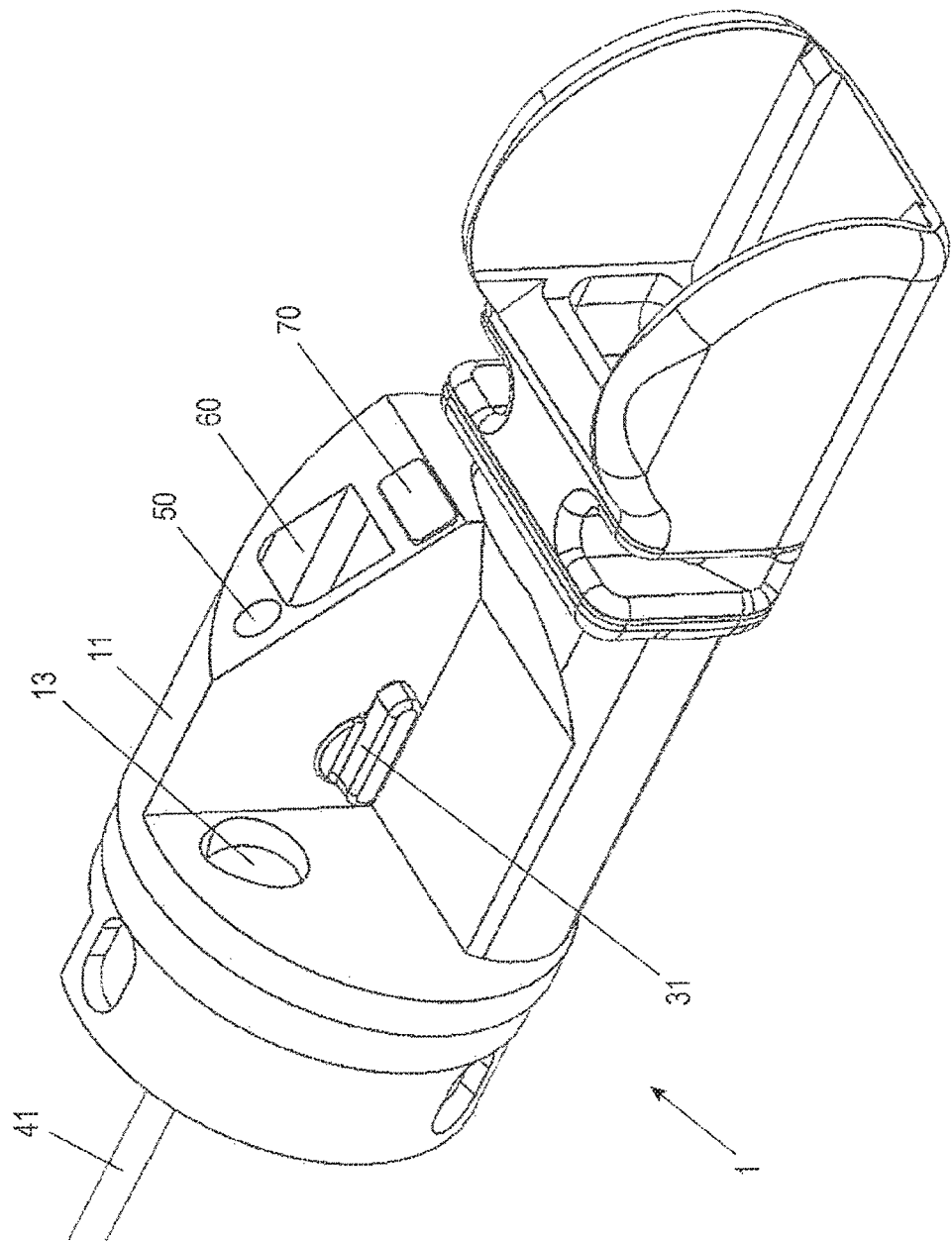
FIG. 4 shows a perspective view of an inventive endoscope head of a second embodiment from the left side in a state in which an Albarran lever has not yet been inserted.

FIG. 4 shows a flat connecting end portion of a pivot axis element 31. An Albarran lever, which comprises a counter-opening corresponding to the flat connecting end portion of the pivot axis element 31, can be pushed onto said flat connecting end portion from the distal side.

The Albarran lever can be controlled in the same way as described in the first embodiment.

Alternatives

In embodiment 1, an ultrasonic element is arranged on the endoscope head 1. The invention is also applicable to an endoscope head without an ultrasonic element, said endoscope head being constructed without an ultrasonic element holder 80.

An urging means, such as e.g. a coil spring, can be arranged on the distal side of the sliding member 43 as a pressing biasing means for urging the sliding member 43 in the proximal direction. By a pulling movement of the pulling wire 42 in the proximal direction, the sliding member 43 is shifted in the distal direction by the spring force of the distal coil spring being overcome.

In an alternative, an urging means, such as a tension spring, can be arranged on the distal side of the sliding member 43 as a pulling biasing means for urging the sliding member 43 in the distal direction.

The shape of the protrusion engaging in the sliding member 43 is not restricted. Moreover, the kind of contact between the sliding member 43 and the force-receiving element 33 is not restricted. Instead as a protrusion 333 in an involute shape, e.g. a rod-shaped protrusion can be formed on the force-receiving element 33, said protrusion being inserted into an opening of the sliding member 43 and being adapted to slide on the sliding member 43. The rod-shaped protrusion can have a comparatively large play to the opening of the sliding member 43. Thus, the protrusion of the pivot member can be formed as a sliding element that is slidingly supported on the surface of the sliding member.

In a further alternative, a rolling wheel can be provided on said rod-shaped protrusion on the force-transmitting element 33, said rolling wheel being rollably in contact with the surface of the sliding member. In this embodiment, too, a translational movement is transformed into a rotational movement, the rotational movement being used for pivoting the Albarran lever.

It is only required that the sliding member 43 is adapted to transmit the force for pivoting the Albarran lever via the force-transducing element. The shape of the force-receiving element is not subject to any restrictions, either.

The shape of the sliding member 43 is no subject to restrictions, either. The only thing one has to take care of is a sufficiently secure guiding of the sliding member 43 in the endoscope head body 11.

In an alternative, the sliding member can be fastened to the pulling wire and the pulling wire can be made to be elastic (flexible). In this case, no pulling wire sleeve 41 is necessary. The control element pulls the pulling wire in the proximal direction and the sliding member is moved in the proximal direction by the elasticity of the pulling wire section which is distal of the sliding member.

The principle of the present invention can be applied to kinds of operations of Albarran levers.

The use of the LED may be replaced by the use of another illumination means, such as a light fiber.

The present invention is applicable with a rigid endoscope as well as with a flexible endoscope. The principle of the present invention can be applied to all types of endoscopes.

The discussed alternatives can be suitably combined.

LIST OF REFERENCE SIGNS 1 endoscope head
11 endoscope head body
13 working channel
30 Albarran lever
31 pivot axis element
33 force-receiving element
40 pulling wire channel
41 pulling wire sleeve
42 pulling wire
43 sliding member
44 pulling wire nipple
50 water nozzle
60 camera
70 illumination means
80 ultrasonic element holder
81 accommodation space for ultrasonic element
114 blind hole for pulling wire nipple
300 working surface
331 force-receiving-element main body
332 opening for pivot axis element
333 protrusion
334 first surface, proximal surface 335 second surface, distal surface
337 opening for locking screw
430 opening for force-receiving element
431 first surface, proximal surface
432 second surface, distal surface

The invention claimed is:

1. An endoscope head comprising an endoscope head body in which a working channel is formed, the endoscope head body comprising:
- a pivotable Albarran lever provided distally of a distal end of the working channel;
- a pivot lever having a protrusion and which is actuatable from a proximal side of the working channel and which is configured to pivot the Albarran lever;
- a pulling wire sleeve extending through a pulling wire channel and having a proximal end and a distal end, the pulling wire sleeve being slidable along an axial direction of the endoscope head body;
- a pulling wire extending through the pulling wire sleeve and fixed along the axial direction of the endoscope head body; and
- slider having a surface on which the protrusion is supported and connected to the distal end of the pulling wire sleeve, wherein when the pulling wire sleeve is pulled from the proximal end in the axial direction of the endoscope head body, the pulling wire sleeve displaces the slider relative to the pulling wire such that the pivot lever is rotated by the displacement of the slider.

2. The endoscope head according to claim 1, wherein the protrusion of the pivot lever has a shape of an involute which is supported on the surface of the slider in a rolling manner.

3. The endoscope head according to claim 1, wherein the slider has a first surface on which a first outer surface of the protrusion is supported, and the slider has a second surface on which a second outer surface of the protrusion is supported.

4. The endoscope head according to claim 3, wherein the slider is configured such that,
- when the pulling wire sleeve is moved in a proximal direction of the endoscope head body, the first surface of the slider has the first outer surface of the protrusion to roll thereon in such a way that the pivot lever pivots the Albarran lever in a first direction, and,
- when the pulling wire sleeve is moved in a distal direction of the endoscope head body, the second surface of the sliding member slider has the second outer surface of the protrusion roll thereon in such a way that the pivot lever pivots the Albarran lever in the a second direction.

5. The endoscope head according to claim 3, wherein,
- at the slider, the first surface and the second surface face each other and,
- at the protrusion, the first outer surface and the second outer surface face in opposite directions.

6. The endoscope head according to claim 1, wherein, the slider is displaceable back and forth by the pulling wire sleeve exclusively in the axial direction of the endoscope head.

7. The endoscope head according to claim 1, wherein a distal end of the pulling wire channel is sealed at the endoscope head body.

8. The endoscope head according to claim 1, wherein a distal end of the pulling wire is anchored to the endoscope head body at an anchoring point, and the sliding member slider is arranged at the pulling wire proximally of the anchoring point.

9. An endoscope comprising the endoscope head according to claim 1.

* * * * *